United States Patent
Yang et al.

(10) Patent No.: US 7,287,420 B2
(45) Date of Patent: Oct. 30, 2007

(54) METHOD OF MEASURING PROPERTIES OF INTERFACIAL ADHESION OF MEDICAL DEVICE COATINGS

(75) Inventors: Dehua Yang, Savage, MN (US); David J. Vodnick, Eden Prairie, MN (US); Richard J. Nay, Shorewood, MN (US); Thomas J. Wyrobek, Edina, MN (US)

(73) Assignee: Hysitron, Inc., Minneapolis, MN (US)

( * ) Notice: Subject to any disclaimer, the term of this patent is extended or adjusted under 35 U.S.C. 154(b) by 0 days.

(21) Appl. No.: 11/316,471

(22) Filed: Dec. 22, 2005

(65) Prior Publication Data

US 2006/0137469 A1  Jun. 29, 2006

(51) Int. Cl.
*G01N 3/48* (2006.01)
*G01N 19/04* (2006.01)

(52) U.S. Cl. .......................... 73/81; 73/150 A
(58) Field of Classification Search .............. 73/81, 73/150 A, 845, 788, 82, 83, 838
See application file for complete search history.

(56) References Cited

U.S. PATENT DOCUMENTS

| | | | |
|---|---|---|---|
| 4,856,326 A | 8/1989 | Tsukamoto | 73/150 A |
| 5,696,327 A | 12/1997 | Huang et al. | 73/845 |
| 6,026,677 A * | 2/2000 | Bonin | 73/105 |
| 6,339,958 B1 | 1/2002 | Tsui et al. | 73/150 A |
| 6,502,455 B1 | 1/2003 | Gitis et al. | 73/150 A |
| 6,945,097 B2 | 9/2005 | Jardret et al. | 73/81 |

OTHER PUBLICATIONS

Volinsky et al., "Interfacial toughness measurements for thin films on substrates,"Acta Materialia Inc., 2002, pp. 441-466.
Zantye et al., "A Study of Interfacial Adhesion of Thin Films for Microelectronics Applications," pp. 1-15.

* cited by examiner

*Primary Examiner*—Hezron Williams
*Assistant Examiner*—Tamiko Bellamy
(74) *Attorney, Agent, or Firm*—Dicke, Billig, & Czaja, P.L.L.C.

(57) ABSTRACT

A method for measuring toughness of interfacial adhesion including applying a normal force with a probe to a surface of a coating joined to a major surface of a substrate of a medical device, wherein the surface is substantially parallel to the major surface, and applying a lateral force to the coating with the probe by laterally moving a position of the probe relative to the major surface such that the probe forms at least one delaminated region in the coating as the position of the probe moves laterally across the major surface, the delaminated region having a starting point and an ending point. The method further includes measuring a magnitude of the lateral force over time, and determining a toughness of interfacial adhesion between the coating and the major surface based on changes in magnitude of the lateral force as the position of the probe moves from the starting point to ending point.

23 Claims, 10 Drawing Sheets

METHOD OF MEASURING PROPERTIES OF INTERFACIAL ADHESION OF MEDICAL DEVICE COATINGS

THE FIELD OF THE INVENTION

The present invention generally relates to a system and a method employing an energy-based approach for measuring toughness of interfacial adhesion between a coating and a medical device to which the coating has been applied.

BACKGROUND OF THE INVENTION

Devices are commonly coated with thin films and other coatings in order to enhance their performance and functionality. Such coatings can be broadly characterized as being either hard coatings or soft coatings. Hard coatings, such as ceramic and diamond-like carbon, for example, are often applied to cutting tools to enhance their cutting ability and durability. Soft coatings, such as polymer-based materials, for example, are often applied to medical devices to improve their bio-compatibility.

For purposes of quality and process control, it is desirable to measure the toughness of the interfacial adhesion, or bond, between the coatings and substrates. Several testing methods are presently employed to measure interfacial adhesion toughness and include the "Pull" or "Stud Pull" test, the "Four-Point Bending" test, the "Tensile" or "Shear" test, the "Bulge" or "Blister test, the "Laser Impact Spallation" test, the "Indentation" test, and the "Scratch" test. However, there is often a lack of agreement in the measurements provided by these different techniques. Additionally, these techniques are not always effective at measuring the interfacial adhesion toughness of coatings applied to substrates having non-planar surfaces or flexible structures, particularly when the coatings comprise soft coatings.

SUMMARY OF THE INVENTION

In one embodiment, the present invention provides a method for measuring toughness of interfacial adhesion. The method includes applying a normal force with a probe to a surface of a coating joined to a major surface of a substrate of a medical device, wherein the surface is substantially parallel to the major surface, and applying a lateral force to the coating with the probe by laterally moving a position of the probe relative to the major surface such that the probe forms at least one delaminated region in the coating as the position of the probe moves laterally across the major surface, the delaminated region having a starting point and an ending point. The method further includes measuring a magnitude of the lateral force over time, and determining a toughness of interfacial adhesion between the coating and the major surface based on changes in magnitude of the lateral force as the position of the probe moves from the starting point to ending point.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be used and structural or logical changes may be made without departing from the scope of the present invention. The following detailed description, therefore, is not to be taken in a limiting sense, and the scope of the present invention is defined by the appended claims.

As described herein, a system and method are provided for measuring the toughness (energy per unit area) of interfacial adhesion between a thin film or coating and a substrate of a medical device to which it is applied. In one embodiment, the system and method includes applying normal and lateral forces to the coating and substrate and measuring a portion of applied energy to determine the work of adhesion to separate or delaminate a portion of the coating from the medical device.

Figure 1:
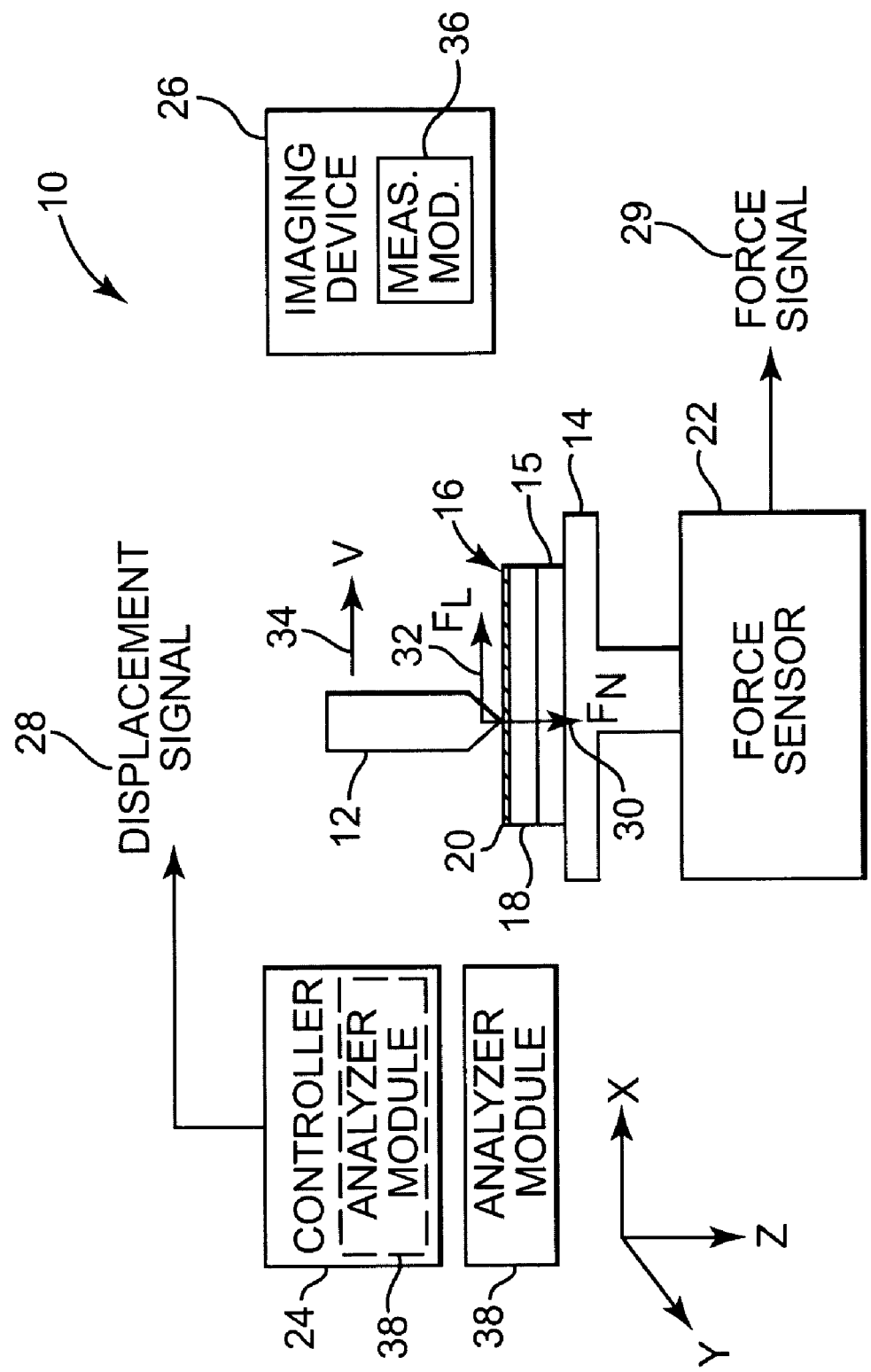
FIG. 1 is a block diagram illustrating one embodiment of a measuring apparatus according to the present invention.

FIG. 1 illustrates one example embodiment of a measuring apparatus 10, according to the present invention, for determining the toughness of interfacial adhesion, or work of adhesion (i.e. energy per unit area), between a thin film and a medical device substrate to which it has been applied. Measuring apparatus 10 includes a scratch probe 12, and a platform 14 configured to hold a medical device 16, or at least a portion or sample of a medical device 16, having a substrate 18 to which a coating or thin-film 20 has been applied. In one embodiment, as illustrated, measuring apparatus 10 further includes a holding device 15 which is selectively coupled to platform 14 and configured to hold and secure device 16 so that it is not damaged prior to testing.

Examples of medical devices include devices that may be used internal or external to the body, such as catheters, biomedical devices, pacemakers, prosthetic implants, and orthopedic biomedical devices, for example. Additionally, measuring apparatus 10 and the energy-based measurement techniques according to the present invention my also be employed to measure interfacial adhesion properties of various type of medical device packaging.

Measuring device 10 further includes a force sensor 22, a controller 24, and an imaging device 26. Controller 24 is configured to control movement of scratch probe 12 in the x, y and z dimensions relative to platform 14, and to provide a displacement signal 28 representative of displacement of scratch probe 12 in said dimensions from an initial reference point. Force sensor 22 is configured to measure a normal force ($F_N$) 30 and a lateral force ($F_L$) 32 between scratch probe 12 and device 16 as scratch probe 12 moves laterally across device 16 at a scratch velocity (V) 34, and to provide a force signal 29 representative of the measured normal and lateral forces 30 and 32.

Measuring apparatus 10 further includes an imaging device 26 or other instrument/device capable of recording or determining the profile or contour of a test region, such as an optical microscope, a profilometer, a scanning probe microscope (SPM) or an atomic force microscope (AFM), and is configured to provide images of coating 20 and substrate 18 of sample 16. One example of an optical viewing device suitable to be configured for use as imaging device 26 is commercially available under the trade name Ziess Axio Imager Microscope from Carl Zeiss Microimaging, Incorporated of Thornwood, N.Y., USA. In one embodiment, as will be described in greater detail below, imaging device 26 includes an optical area measurement module 36 for automatically measuring an area of a user defined region.

Examples of systems similar to measuring apparatus 10 and suitable to be configured for use with the present invention are described by U.S. Pat. Nos. 5,553,486 and 5,869,751, both of which are assigned to the same assignee as the present invention and are incorporated by reference herein. Another test system suitable to be configured for use with this invention is commercially available under the tradename TriboIndenter from Hysitron Incorporated of Minneapolis, Minn., USA.

According to one embodiment of the present invention, measuring apparatus 10 is configured to perform an adhesion test, similar in nature to a "scratch" test, to measure the interfacial toughness, or work of adhesion, between coating 20 and substrate 18 to which it is joined. In one embodiment, controller 24 initially positions scratch probe 12 proximate to or in contact with coating 20 at a desired location on device 16. For example, in one instance, as illustrated by FIG. 2 below, it may be desirable to position scratch probe 12 away from edge locations of substrate 18, while in other instances, it may be desirable to position scratch probe 12 proximate to edges of substrate 18.

Figure 2:
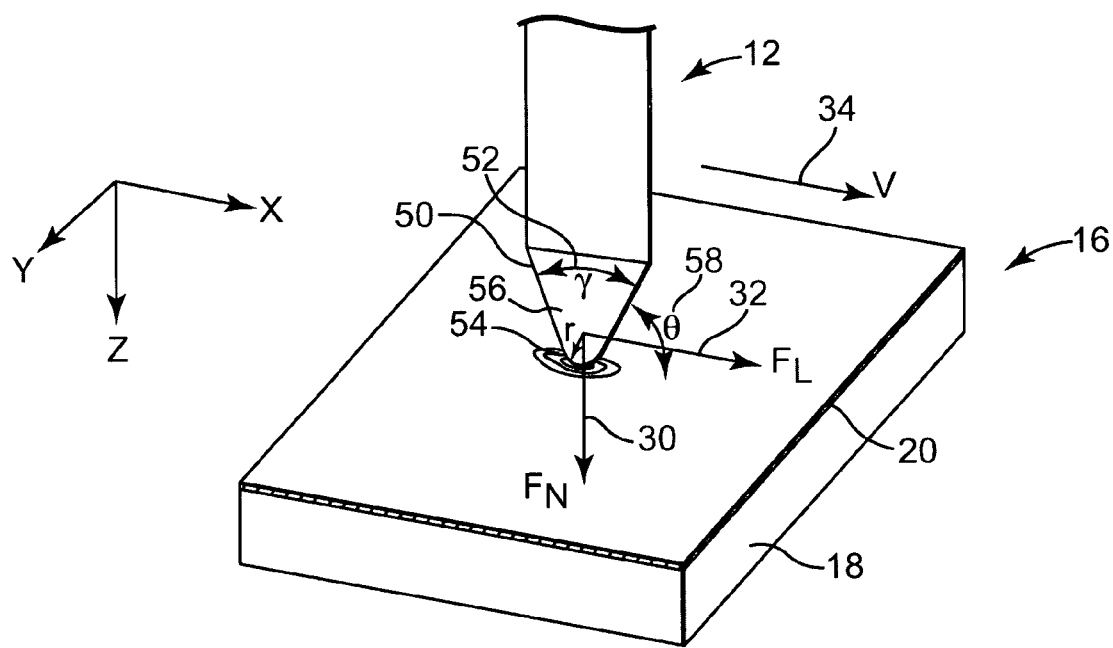
FIG. 2 is a perspective view of one embodiment of a scratch probe engaging a coating on a device.

FIG. 2 is a perspective view illustrating generally portions of one embodiment of scratch probe 12 in contact with a medical device 16. In one embodiment, as illustrated, scratch probe 12 comprises a cono-spherical probe having a cone-shaped portion 50 having an angle (γ) 52 and a spherical tip 54 having a radius (r) 56 for scratching and delaminating coating 20 of device 16. In one embodiment, angle 52 is approximately 60 degrees and radius 56 is approximately 5 micrometers (μm). In one embodiment, angle 52 is approximately 60 degrees and radius 56 is approximately 20 μm. Although described primarily herein in terms of having a cono-spherical configuration, scratch probe 12 can be of any axis-symmetric configuration, such as conical or spherical, for example.

In one embodiment, after initial positioning of scratch probe 12, controller 24 moves scratch probe 12 in the z-direction (downward toward platform 14 with respect to FIG. 1) so as to cause scratch probe 12 to apply normal force ($F_N$) 30 to device 16. In one embodiment, normal force 30 comprises a force which increases over time (e.g. a ramp-like force). In one exemplary embodiment, as will be described in greater detail below, normal force 30 comprises a substantially constant force or load.

In one embodiment, concurrent with applying normal force 30, scratch probe 12 and platform 14 are moved laterally to one another (x-direction) at scratch velocity 34 so as to cause scratch probe 12 to apply lateral force ($F_L$) 32 to device 16. In one embodiment, controller 24 causes scratch probe 12 to move laterally across device 16 by controlling lateral movement of scratch probe 12 while platform 14 remains laterally stationary. Conversely, in an alternate embodiment, controller 24 causes scratch probe 12 to move laterally across device 16 by controlling lateral movement of platform 14 while scratch probe 12 remains laterally stationary.

As scratch probe 12 moves laterally across device 16, force sensor 22 measures normal and lateral forces 30 and 32 between scratch probe 12 and device 16 and provides force signal 29 indicative of the measured values of normal and lateral forces 30 and 32. Concurrently, controller 24 provides displacement signal 28 indicative of the normal (z-direction) and lateral displacement (x-direction) of scratch probe 12 relative to device 16. In one embodiment, controller 24 controls scratch probe 12 such that scratch probe 12 applies normal force 30 at a desired constant load to device 16. As will be described in greater detail below, the desired constant normal load may vary depending upon various factors associated with coating 20 and may need to be adjusted depending upon a particular device 16 being tested.

In one embodiment, controller 24 brings normal force 30 from an unload condition (i.e. no load) to the desired constant load and maintains normal force 30 substantially at the desired constant load for a duration of a scratch operation. At the conclusion of the scratch operation, controller 24 returns normal force 30 from the desired constant load to an unload condition in an unload time. In one embodiment, the load and unload times each comprise approximately 0.1 seconds.

Figure 3A:
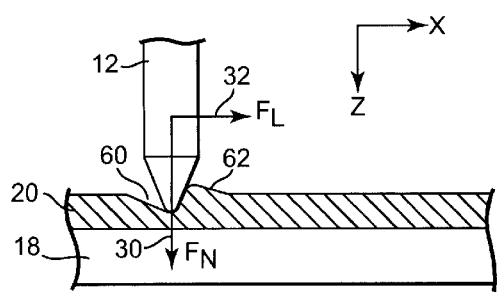
FIGS. 3A-3F are cross-sectional views illustrating generally lateral movement of a scratch probe engaging a coating on a device.

FIGS. 3A-3F are cross-sectional views illustrating portions of device 16 being contacted and scratched by scratch probe 12 during a portion of a scratch operation. Referring first to FIG. 3A, as scratch probe 12 moves laterally across device 16 and normal force 30 is brought to the desired constant load, scratch probe 12 begins to penetrate and deform a portion of coating 20, as shown at 60. Additionally, as scratch probe 12 moves laterally (x-direction as shown), lateral force 32 begins to increase as coating 20 begins to "bunch up" in front of scratch probe 12, as shown at 62.

Figure 3B:
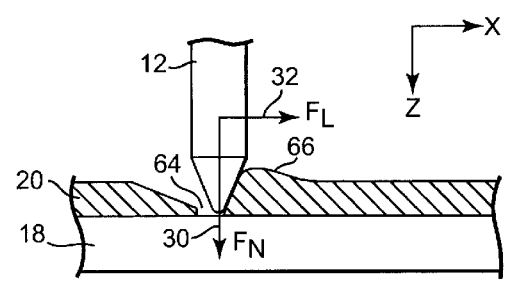

With reference to FIG. 3B, as scratch probe 12 continues to move laterally, lateral force 32 reaches a critical load at which point coating 20 is initially fractured or separated from substrate 18, as shown at 64. Also, as indicated at 66, coating 20 continues to pile-up and be pushed ahead of scratch probe 12.

Figure 3C:
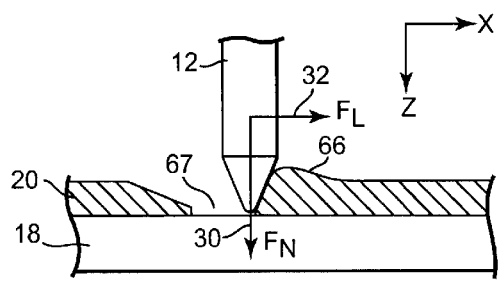

With reference to FIG. 3C, as scratch probe 12 continues to move laterally across device 16, scratch probe 12 continues to delaminate a portion of coating 20 from substrate 18 and to tear the delaminated portion of coating 20 from adjacent portions of coating 20 and begins to form a delaminated region having an increasing area, as shown at 67.

Figure 3D:
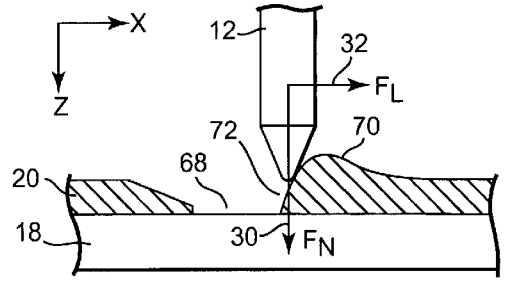

With reference to FIG. 3D, as scratch probe 12 continues to move laterally across device 16, the piled-up coating 20 in front of scratch probe 12, as illustrated at 70, reaches an amount which can no longer be pushed forward by scratch probe 12. At this point, scratch probe 12 is no longer able to delaminate coating 20 from substrate 18 and the area of the delaminated region 68 no longer continues to increase. Instead, as scratch probe 12 continues to move laterally, scratch probe 12 begins to "climb over" piled-up coating 70, as indicated at 72.

Figure 3F:
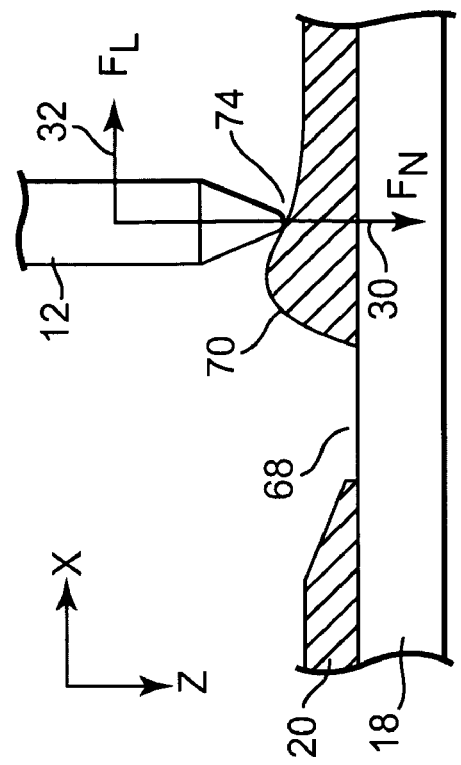
Figure 3E:
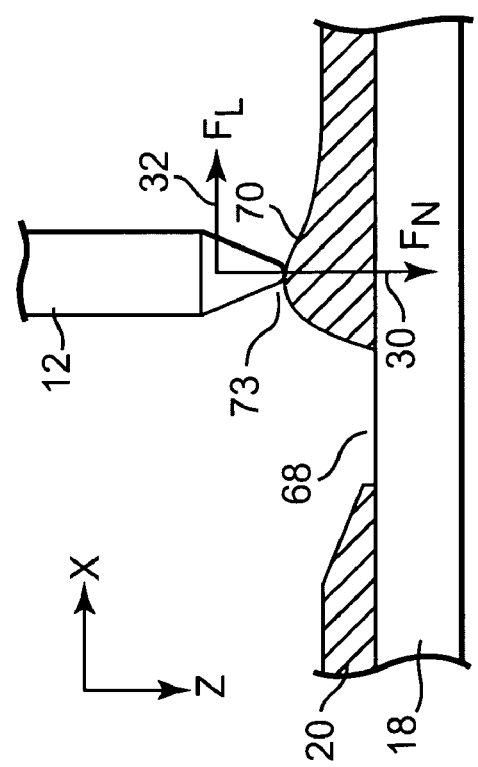

With reference to FIGS. 3E and 3F, as scratch probe 12 continues to move laterally, scratch probe 12 reaches the peak of piled up coating 70, as indicated at 73, and ultimately moves down the opposite side of piled-up coating 70, as indicated at 74. In one embodiment, as will be described in greater detail below, the above described process illustrated by FIGS. 3A-3F is repeated, with scratch probe 12 creating a series of delaminated areas in coating 20, similar to delaminated region 68, as scratch probe 12 moves laterally across device 16.

As described above, as scratch probe moves across device 16, force sensor 22 measures normal and lateral forces 30 and 32 between scratch probe 12 and device 16, and controller 24 measures the normal and lateral displacement of scratch probe 12 relative to device 16. In one embodiment, as will be described in greater detail below, force sensor 22 provides the measured values of normal and lateral forces 30 and 32 at force signal 29 in the form of force versus time plots. Similarly, in one embodiment, controller 24 provides measured values of normal and lateral displacement of scratch probe 12 at displacement signal 28 in the form of distance versus time plots.

Additionally, imaging device 26 provides to-scale images of device 16 which illustrate any delaminated regions of coating 20, such as delaminated region 68 illustrated by FIGS. 3D-3F. In one embodiment, a user defines the boundaries of a delaminated region of coating 20 via measurement module 36, and measurement module 36 automatically calculates the area of the user defined delaminated region.

In one embodiment, as will be described in greater detail below, an amount of "interfacial" energy required to separate or delaminate coating 20 from substrate 18 to create a delaminated region, such as delaminated region 68 (see FIGS. 3D-3F), is determined based on a selected portion of the measured values of lateral force 32 provided by force sensor 22. In one embodiment, as will be described in greater detail below, the selected portion of the measured values of lateral force 32 comprises those values measured by force sensor 22 as scratch probe 12 moves from a starting point, which corresponds to the initial fracture point of coating 20 from substrate 18 (as illustrated by FIG. 3B), to an ending point, which corresponds to the point where scratch probe 12 no longer delaminates coating 20 from substrate 18 (as illustrated by FIG. 3D).

As will be described in greater detail below with respect to FIG. 7, only the increases in the measured values of lateral force 32 as scratch probe 12 moves from the starting point to the ending point relative to the measured value of lateral force 32 when scratch probe is at the starting point are attributable to the delaminating of coating 20 from substrate 18 in the formation of delaminated region 68. The remaining portion of the measured values of lateral force 32 are attributable to tearing the delaminated portion of coating 20 from unaffected portions of the coating and to friction between scratch probe 12 and substrate 18. As such, in one embodiment, the interfacial energy is determined based on the increases in the measured values of lateral force 32 provided by force sensor 22 as scratch probe 12 moves from the starting point to the ending point.

The toughness of interfacial adhesion between coating 20 and substrate 18 is then determined by dividing the above determined interfacial energy by the area of delaminated region 68 as measured by measurement module 36. In one embodiment, with reference to FIG. 1, measuring apparatus 10 further includes an analyzer module 38 configured to receive the displacement signal 28, force signal 29, and the area measurement from measurement module 36, and configured to determine the toughness of interfacial adhesion as described above and as will be described in greater detail below with respect to Equations II-IV and FIGS. 4A-7. In one embodiment, analyzer module 38 comprises a portion of controller 24, as illustrated by the dashed lines in FIG. 1.

As briefly described above, in one embodiment, scratch probe 12 is moved laterally across device 16 such that the process described and illustrated by FIGS. 3A-3F is repeated and a series of delaminated areas, similar to delaminated region 68, are created as scratch probe 12 moves across device 16. In such an embodiment, a toughness of interfacial adhesion is determined (as briefly described above) for each of a selected portion of delaminated areas of the series of delaminated areas and a toughness of interfacial adhesion between coating 20 and substrate 18 is determined based on an average of the toughness of interfacial adhesion of the selected portion of delaminated areas.

In summary, by employing a cono-spherical configuration or axis-symmetrical configuration for scratch probe 12 and the energy-based measurement techniques as described herein, measuring apparatus 10 is well-suited to determine the toughness of interfacial adhesion of soft coatings applied to hard surfaces, to small surfaces, and to non-planar or other irregular surfaces (e.g. curved surfaces) which do not lend themselves to be consistently or accurately tested by presently known techniques and systems. By determining interfacial energy required to delaminate a portion of the coating from the substrate based on a selected portion of measured values of lateral force as described herein, measuring apparatus 10 and energy-based measurement techniques in accordance with the present invention provide accurate and effective measurement of the toughness of interfacial adhesion of soft coatings applied to such surfaces relative to known measuring techniques and systems. In particular, the measuring apparatus and energy-based measurement techniques of the present invention are suitable for measuring the toughness of interfacial adhesion of coatings applied to medical devices.

Furthermore, measuring apparatus 10 and energy-based measurement techniques according to the present invention do not require specially prepared samples or modified devices for testing. As such, measuring apparatus 10 and the energy-based measurement techniques of the present invention are suitable for in-situ and on-part/product testing, and may be part of a laboratory research or a production product testing/quality control process.

FIGS. 4A-6 below describe an example of the operation of one embodiment of the present invention for determining the toughness of interfacial adhesion between a coating and a substrate to which it has been applied. In the example, device 16 includes a coating 20 comprising a 2 $\mu$m thick "parylene C" coating applied to a substrate 18 comprising type 304 stainless steel. In this example, substrate 18 comprises a type 304 stainless steel tube, as illustrated by FIG. 2. Parylene C is an inert, hydrophobic, optically clear biocompatible polymer coating material used in a wide variety of industries and applications.

Although described and illustrated herein primarily in terms of a soft coating (e.g Parylene C) on a metal substrate (e.g. stainless steel), other types of coatings and substrates and combinations thereof may also be tested. For example, medical devices having metallic and/or non-metallic substrates (e.g. copper, aluminum, silicon, silicon nitride, polymers, ceramic, glass) and coatings of materials having insulating and/or non-insulating properties may also be tested.

In the illustrations described by FIGS. 4A-6 below, normal force 30 comprises a substantially constant 15,000 micro-Newton (μN) load applied to device 16 using a scratch probe 12 having a 60-degree angle 52 and a 5 μm tip radius 56 (see FIG. 2) and is moved laterally relative to device 16 at a constant velocity of approximately 10 μm/second over a scratch distance of approximately 500 μm.

Figure 4A:
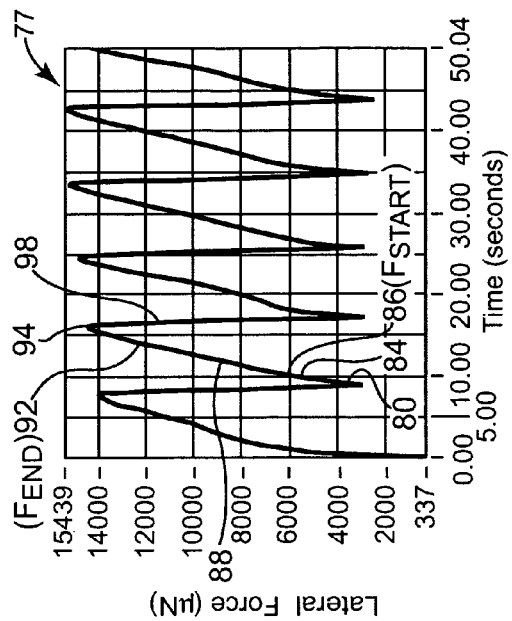
FIG. 4A is a graph of a normal force versus time on a scratch probe.
Figure 4B:
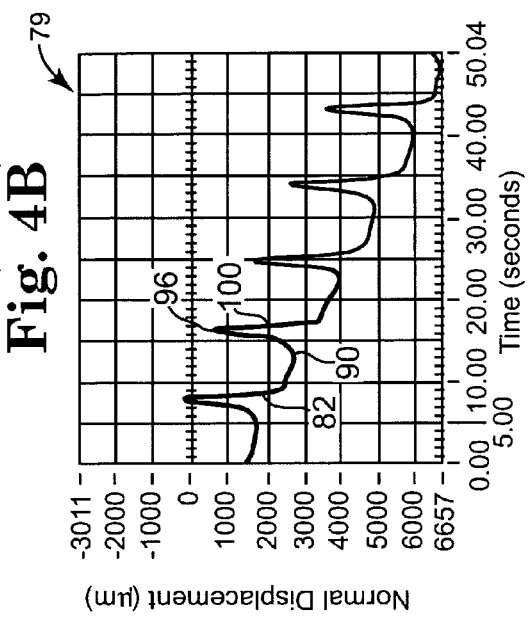
FIG. 4B is a graph of a lateral force versus time on a scratch probe.
Figure 5A:
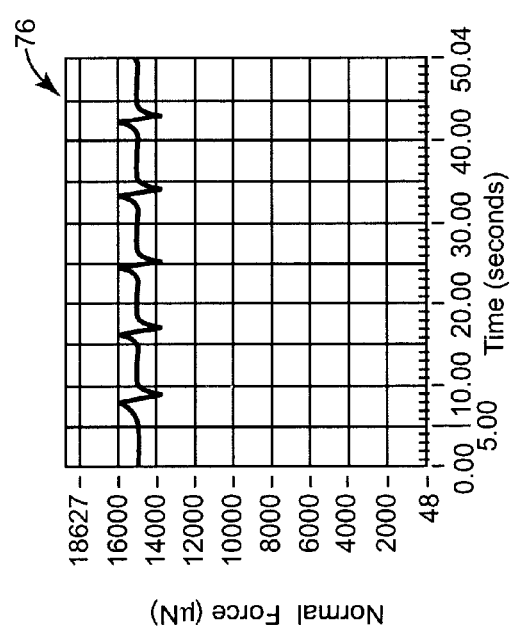
FIG. 5A is a graph of lateral displacement versus time of a scratch probe.
Figure 5B:
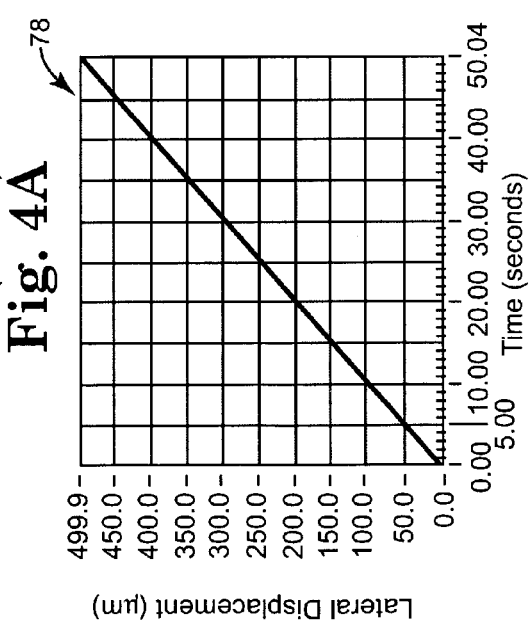
FIG. 5B is a graph of normal displacement versus time of a scratch probe.

FIGS. 4A and 4B are graphs 76 and 77 respectively illustrating normal and lateral forces 30 and 32 versus time as measured and provided by force sensor 22 as scratch probe 12 moves laterally (x-direction with respect to FIGS. 3A-3D) across device 16. FIGS. 5A and 5B are graphs 78 and 79 respectively illustrating lateral and normal displacement of scratch probe 12 versus time as measured and provided by controller 24 as scratch probe 12 moves laterally across device 16. With reference to FIG. 5B, it is noted that a normal displacement of "0" at time "0" represents the initial starting point or reference point of tip 54 of scratch probe 12 at the surface of coating 20 of device 16.

With reference to FIGS. 5A and 5B, when normal force 30 is applied to scratch probe 12 and scratch probe 12 is moved laterally across device 16, lateral force 32 begins to increase, as indicated at 80. Concurrently, the normal displacement begins to move downward, as indicated at 82, as scratch probe 12 begins to penetrate coating 20. This corresponds approximately to the position of scratch probe 12 as illustrated by FIG. 3A.

As scratch probe 12 continues to move laterally and downward, lateral force 32 continues to increase at generally a first slope, as indicated at 84, until it reaches a critical load at which point coating 20 initially "fractures" and separates from substrate 18, as indicated at point 86 in FIG. 4B. This corresponds approximately to the position of scratch probe 12 as illustrated by FIG. 3B.

After the initial fracture of coating 20, lateral force 32 increases at generally a second slope, as indicated at 88, as scratch probe 12 continues to move laterally and tears the separated coating from adjoining unaffected areas and delaminates the torn portion of coating 20 from substrate 18. This slope change produces a "kink" in the graph of lateral force 32 at point 86 and is referred to and labeled as $F_{START}$. This corresponds approximately to the position of scratch probe 12 as illustrated by FIG. 3B.

As scratch probe 12 continues to move laterally across device 16, lateral force 32 continues to increase at generally the second slope until an amount of separated coating 20 accumulates in front of scratch probe 12 such that scratch probe 12 is unable to delaminate any additional amount of coating 20. At this point, the normal displacement of scratch probe 12 reaches a local "valley" and begins to move upward, as indicated at point 90 in FIG. 5B. As scratch probe 12 begins to "climb" over the piled-up coating, the progression of delamination stops. The corresponding lateral force 32 at this point is indicated as point 92 in FIG. 4B and is referred to and labeled as $F_{END}$. This corresponds approximately to the position of scratch probe 12 as illustrated by FIG. 3D.

Lateral force 32 continues to increase as scratch probe 12 climbs up the piled-up coating until it reaches a local peak, as indicated at 94, which is prior to a local upward peak 96 in the normal displacement of scratch probe 12 when scratch probe 12 reaches a peak of the piled-up coating. This corresponds approximately to the position of scratch probe 12 as indicated by FIG. 3E. As scratch probe 12 crosses the peak of the piled-up coating and begins to move down the other side, lateral force 32 quickly drops, as indicated at 98, as does the normal displacement, as indicated at 100. This corresponds approximately to the position of scratch probe 12 as indicated by FIG. 3F.

The above described process is repeated as scratch probe 12 continues to move laterally across device 16 over the 500 μm scratch track resulting in the oscillating nature of the graphs of lateral force 32 and normal displacement of scratch probe 12 respectively illustrated by FIGS. 4B and 5B. Each oscillation represents a delamination cycle which corresponds to a separate delaminated region (e.g. delaminated region 68 illustrated by FIGS. 3D-3F) of a series of delaminated regions of coating 20 from substrate 18 created by scratch probe 12 as it moves laterally across device 16 during a scratch operation. It is noted that the overall downward trend of the normal displacement of scratch probe 12 illustrated by FIG. 5B results from device 16 being positioned at an angle (i.e. $\theta+\gamma/2 \neq 90$ degrees) with respect to scratch probe 12, as illustrated in FIG. 2.

Figure 6:
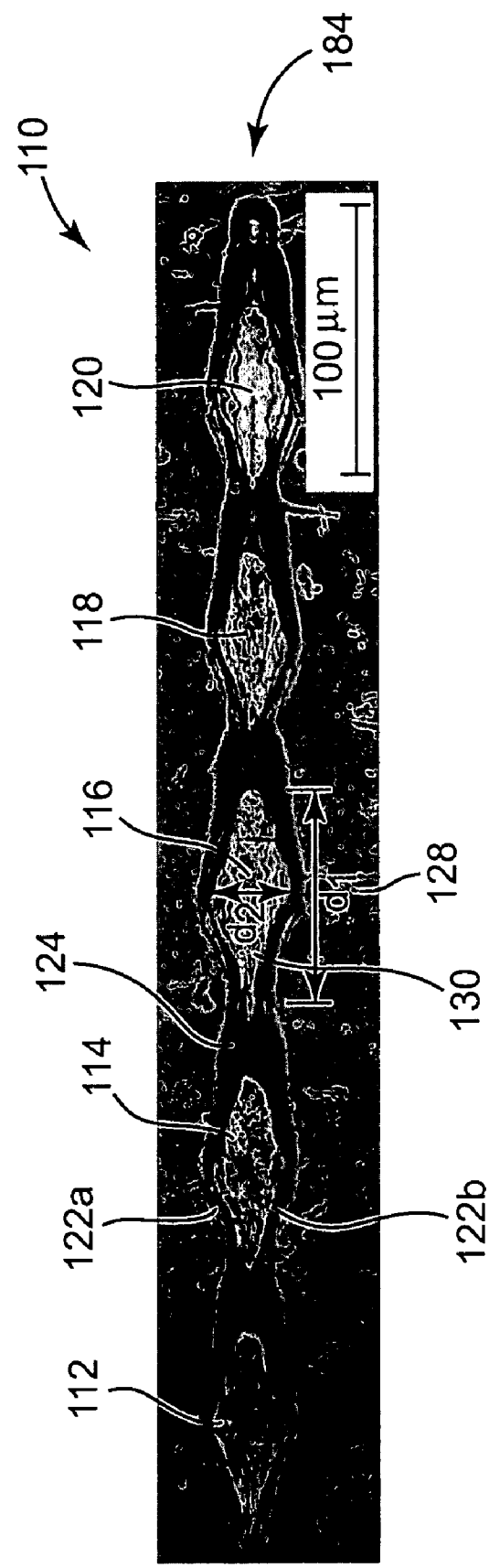
FIG. 6 is an image of a scratch track in a coating on a device.

FIG. 6 is an image provided by imaging device 26 which is representative of a scratch track 110 caused by application of the 15,000 μN normal force 30 and lateral movement of scratch probe 12 across device 16 as described above with respect to FIGS. 4A-5B. Scratch track 110 comprises a series of delaminated regions 112, 114, 116, 118, and 120 where coating 20 has been delaminated from substrate 18 by scratch probe 12 during a scratch operation, wherein each delaminated region appears as diamond-like shape which is lighter in color than adjacent areas.

With respect to delaminated region 114, darker regions 122a and 122b along the edges of delaminated region 114 illustrate where the delaminated portion of coating 20 has been torn away from and distorted adjacent remaining areas of coating 20. Darker region 124 illustrates where the delaminated portion of coating 20 has piled-up and distorted the area of coating 20 in front of scratch probe 12 (similar to that indicated at 70 in FIGS. 3D-3F).

As is typical of each of the delaminated regions illustrated by scratch track 110, delaminated region 116 is substantially diamond-like in shape, having a length (d1) 128 and a width (d2) 130. In one embodiment, to measure the area of a delaminated region, such as delaminated region 116, a user defines the diamond-like shaped region via imaging device 26, the area of which is subsequently calculated by measurement module 36. In one embodiment, based on the diamond-like shape, measurement module 36 calculates the area based on the following Equation I:

$$A=(d1*d2)/2; \text{ where:} \qquad \text{Equation I:}$$

A=area of delaminated region;
d1=length of delaminated region; and
d2=width of delaminated region.

Figure 7:
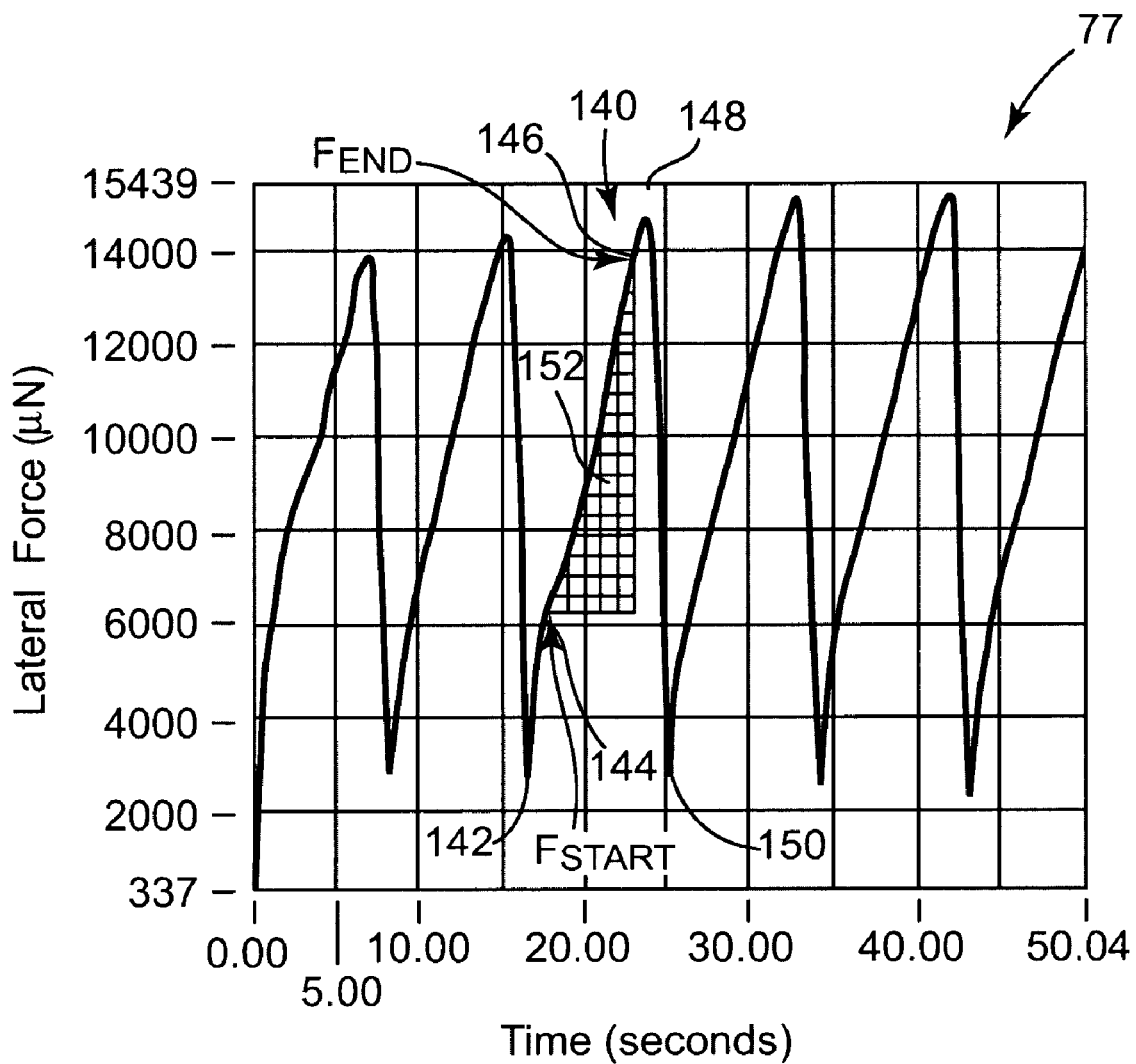
FIG. 7 is an enlarged version of the graph of FIG. 4B.

FIG. 7 is an enlarged version of graph 77 of lateral force 32 illustrated by FIG. 4B and describes an example of a process for determining an amount of energy required to delaminate a region of coating 20 from substrate 18. An oscillation or delamination cycle 140 corresponding to delaminated region 116, as illustrated by FIG. 6, begins at point 142. The "kink" in the curve of lateral force 32 for delamination cycle 140 is indicated at 144 and is labeled as $F_{START}$. The point on the plot of lateral force 32 corresponding to the end of delamination for delamination cycle 140 is indicated at 146 and is labeled as $F_{END}$. $F_{START}$ 144 and $F_{END}$ 146 are similar to points 86 and 92 previously described with regard to graph 77 of FIG. 4B. A local peak of lateral force 32 for scratch cycle 140, as illustrated at point 148, corresponds approximately to a position of scratch probe 12 before it climbs over and reaches a top of an amount of piled up coating 20 in front of scratch probe 12, as illustrated by FIG. 3E. Point 150 marks the end of scratch cycle 140 and a beginning point of a next scratch cycle corresponding to delaminated region 116 (see FIG. 6).

The area below the curve of lateral force 32 from point 142 to $F_{START}$ 144 multiplied by scratch velocity (V) 34 substantially represents the energy supplied by scratch probe 12 to scratch and initially "fracture" coating 20. Energy provided by scratch probe 12 to device 16 in this region of the curve for lateral force 32 is also consumed by frictional forces since scratch probe 12 has relative motion with respect to device 16. As such, the energy supplied by scratch probe 12 from point 142 to $F_{START}$ 144 corresponds to scratch probe 12 reaching a position represented by FIG. 3B.

The area below the curve of lateral force 32 between $F_{START}$ 144 and $F_{END}$ 146 multiplied by scratch velocity (V) 34 represents the total energy ($E_{TOTAL}$) supplied by scratch probe 12 to device 16 to tear and delaminate coating 20 from substrate 18, which corresponds approximately to the lateral movement of scratch probe 12 as illustrated generally above by FIGS. 3B-3D. It may include the frictional energy consumed due to relative motion and contact between scratch probe 12 and substrate 18. The area below the curve of lateral force 32 after $F_{END}$ 146 to point 150 multiplied by scratch velocity (V) 34 represents the energy supplied by scratch probe 12 as it climbs "up and over" piled up coating 20 in front of scratch probe 12, which corresponds approximately to the lateral movement of scratch probe 12 as illustrated generally above by FIGS. 3E-3F.

The total energy ($E_{TOTAL}$) supplied by scratch probe 12 between $F_{START}$ 144 and $F_{END}$ 146 to create the delaminated region, such as delaminated region 116, is consumed in various ways and can be generally described by the following Equation II:

$$E_{TOTAL} = E_{INTERFACIAL} + E_{TEARING} + E_{FRICTIONAL}; \text{ where:} \quad \text{Equation I:}$$

$E_{TOTAL}$=total energy to create delaminated region;
$E_{INTERFACIAL}$=energy consumed to delaminate coating from substrate;
$E_{TEARING}$=energy consumed to tear delaminated coating from unaffected areas; and
$E_{FRICTIONAL}$=energy consumed by contact and relative motion between scratch probe 12 and substrate 18.

As described above, the energy supplied by scratch probe 12 from point 142 to $F_{START}$ 144 represents the energy required for scratch probe 12 to scratch and initially "fracture" coating 20. Once coating 20 begins to tear away from unaffected adjacent areas of coating 20 at $F_{START}$ 144, such as along edges 122a and 122b as illustrated with respect to delaminated region 114 of FIG. 6, the energy required to maintain tearing of coating 20, $E_{TEARING}$, remains substantially constant. Additionally, when normal force 30 comprises a substantially constant force, any frictional energy that may be present between scratch probe 12 and substrate 18, $E_{FRICTIONAL}$, also remains substantially constant from $F_{START}$ 144 to $F_{END}$ 146.

In light of the above, the increase in the level of lateral force 32 from $F_{START}$ 144 to $F_{END}$ 146 represents the force required to delaminate coating 20 from substrate 18 to create delaminated region 116. Accordingly, an area of a triangular cross-hatched region 152 multiplied by scratch velocity (V) 34 represents the amount of interfacial energy, $E_{INTERFACIAL}$, consumed to delaminate coating 20 from substrate 18 to create delaminated region 116. In one embodiment, the interfacial energy, $E_{INTERFACIAL}$, is calculated according to the following Equation III:

Equation III:

$$E_{INTERFACIAL} = \sum_{i=F_{Start}}^{F_{End}} \left[ (x_{i+1} - x_i) \times \left( \frac{F_i + F_{i+1}}{2} - F_{Start} \right) \right]$$

$E_{INTERFACIAL}$=energy consumed to delaminate coating from delaminated region;
i=individual data point;
$F_i$=lateral force at the $i^{th}$ data point;
$F_{(i+1)}$=lateral force at the $i^{th}$ plus one data point;
$F_{START}$=lateral force at beginning of individual delaminated region;
$F_{END}$=lateral force at end of individual; delaminated region;
$x_i$=lateral displacement at the $i^{th}$ data point and described by: $t_i$ x V;
$x_{i+1}$=lateral displacement at the $i^{th}$ plus one data point and described by: $t_{i+1}$ x V;
$t_i$=time at the $i^{th}$ data point;
$t_{i+1}$ time at the $i^{th}$ plus one data point; and
V=scratch velocity.

The toughness of interfacial adhesion (G) between coating 20 and substrate 18 of a delaminated region, such as delaminated region 116, is determined by dividing the interfacial energy calculated based on Equation III by the area of the delaminated region calculated as described above using FIG. 6 and Equation I. As such, the toughness of interfacial adhesion (G) is calculated according to the following Equation IV:

$$G = E_{INTERFACIAL}/A; \text{ where:} \quad \text{Equation IV:}$$

G=toughness of interfacial adhesion of delaminated region;
$E_{INTERFACIAL}$=interfacial energy associated with delaminated region;
A=area of delaminated region.

It is noted that the toughness of interfacial adhesion is sometimes also referred to as the "practical work of adhesion."

In one embodiment, as illustrated by the image of FIG. 6 above, a scratch operation includes applying normal and lateral forces 30 and 32 along a desired scratch track to create a series of delaminated regions, such as delaminated regions 112, 114, 116, 118, and 120 along scratch track 110. In one embodiment, the toughness of interfacial adhesion (G) is calculated as described above for each of the individual delaminated regions, and the toughness of interfacial adhesion between coating 20 and substrate 18 for device 16 comprises an average of the toughness of interfacial adhesion of all of the individual delaminated regions. In one embodiment, to eliminate any potential anomalies that may be introduced by initially applying and subsequently removing normal and lateral forces 30 and 32 from device 16, the first and last delaminated regions of a scratch track are not included when calculating the toughness of interfacial adhesion between coating 20 and substrate 18 based on an average of the toughness of interfacial adhesion of a series of delaminated regions. For example, with respect to FIG. 6, the toughness of interfacial adhesion between coating 20 and substrate 18 is based on an average of the toughness of interfacial adhesion of delaminated regions 114, 116, and 118, with the toughness of interfacial adhesion of delaminated regions 112 and 120 not being included in the calculation.

Figure 8A:
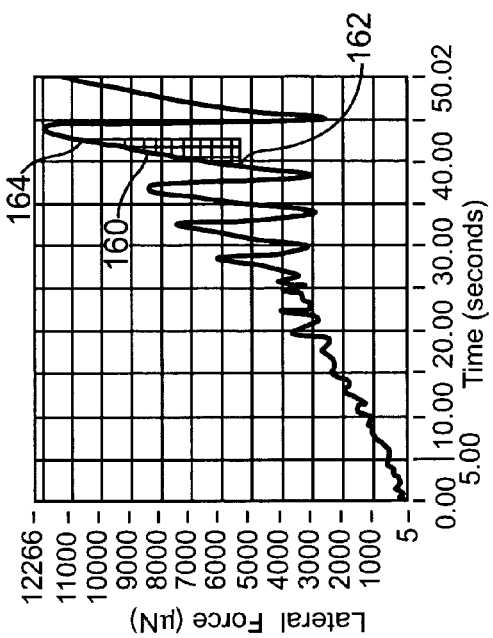
FIG. 8A is a graph of a normal force versus time on a scratch probe.

Although described above primarily as being a substantially constant force, normal force 30 may also comprise a force which varies over time. In one embodiment, normal force 30 comprises a ramp-like force which increases substantially linearly during a scratch operation. For example, FIGS. 8A though 8B respectively illustrate graphs of the normal and lateral forces 30 and 32 with respect to time, and graphs 9A and 9B respectively illustrate graphs of lateral and normal displacement with respect to time as scratch probe 12 moves laterally across device 16 normal force 30 comprises a ramped force 30. As illustrated by FIG. 8A, normal force 30 is a ramp force which increases from an unload condition to approximately 15,000 μN as scratch probe 12 moves laterally across device 16 at a velocity of approximately 10 μm/second.

Figure 8B:
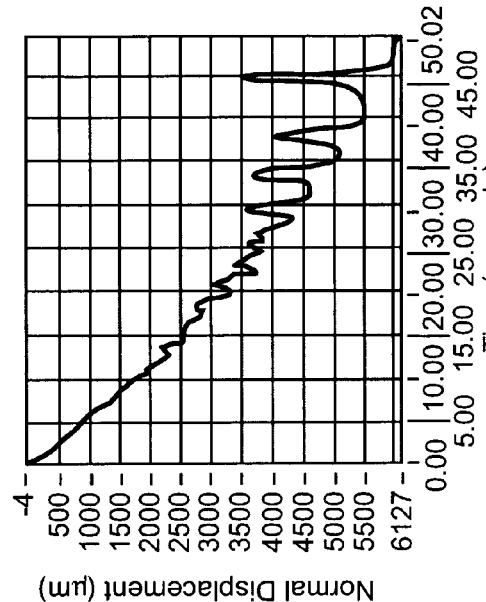
FIG. 8B is a graph of a lateral force versus time on a scratch probe.
Figure 9A:
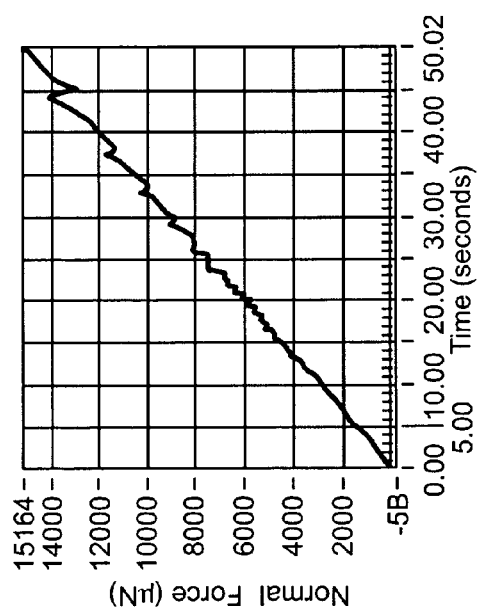
FIG. 9A is a graph of lateral displacement versus time of a scratch probe.
Figure 9B:
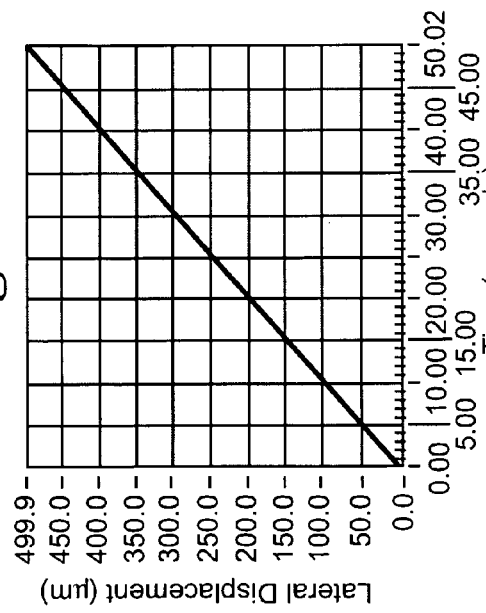
FIG. 9B is a graph of normal displacement versus time of a scratch probe.

Similar to that described above with respect to FIGS. 4B and 5B, the graphs of lateral force 32 and normal displacement illustrated by FIGS. 8B and 9B have an oscillating type pattern as scratch probe 12 moves across device 16, with each oscillation corresponding to an individual delaminated region. The toughness of interfacial adhesion for an individual delaminated region is calculated in a fashion similar to that described above, with the interfacial energy ($E_{INTERFACIAL}$) being approximately equal to the area of a triangular region below the curve of lateral force 32 between $F_{START}$ and $F_{END}$, such as triangular region 160 between $F_{START}$ and $F_{END}$ 162 and 164 multiplied by scratch velocity (V) 34. The generally upward trend of the graph of lateral force 32 illustrated by FIG. 8B is due generally to increasing frictional forces between scratch probe 12 and substrate 18 of device 16 as normal force 30 increases.

As mentioned above with respect to FIG. 2, a desired load to employ as normal force 30 so as to effectively delaminate coating 20 from substrate 18 may vary between devices 16 to be tested depending on factors such as, for example, the mechanical properties of the material employed for coating 20, the thickness of coating 20, and the toughness of interfacial adhesion between coating 20 and substrate 18. However, normal force 30 must be applied at least at a minimum level required to cause coating 20 to delaminate from substrate 18.

In one embodiment, to determine a desired constant scratch load to be utilized for normal force 30, a scratch operation is first performed on device 16 using a ramp load for normal force 30, wherein normal force 30 is increased from zero to a selected maximum load over the duration of the scratch operation. Images of coating 20 provided by imaging device 26 and displacement and force signals 28 and 29 respectively provided by controller 24 and force sensor 22 are analyzed to approximately determine a minimum level of normal force 30 at which coating 20 delaminates from substrate 18. Normal force 30 is then applied at plurality of levels, beginning with the minimum level determined above, and scratch probe 12 is moved at different velocities (see FIG. 1) laterally relative to device 16 so as to create a plurality of scratch tracks so as to determine a desired constant load at which to apply normal force 30 and scratch velocity 34.

In one embodiment, a normal load and velocity which results in scratch probe 12 generating a scratch track having a desired number of delaminated regions over a predetermined track length in coating 20 of device 16 are selected as the desired constant normal load to be applied to scratch tip 12 for testing the toughness of interfacial adhesion between coating 20 and substrate 18 of device 16. In one embodiment, the desired number of delaminated regions is between three and five delaminated regions.

Figure 10:
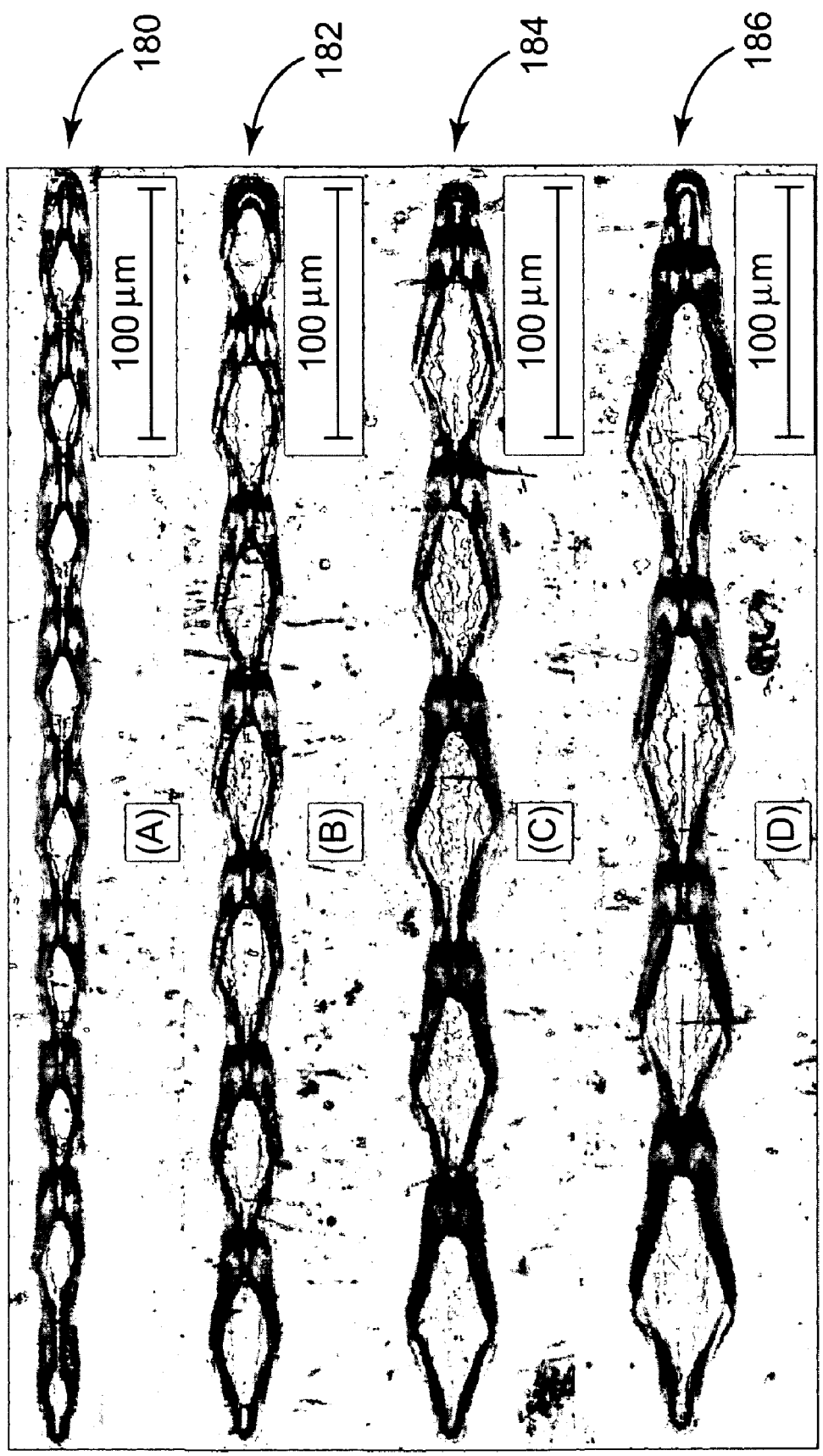
FIG. 10 illustrates images of multiple scratch tracks in a device coating.

As an example, FIG. 10 illustrates optical micrographs generated by imaging device 26 for various scratch tracks produced in coating 20 of a device 16 by scratch probe 12 with normal load 30 at different constant normal loads. Similar to that illustrated by FIG. 6, device 16 includes a coating 20 comprising parylene C and a substrate 18 comprising Type 304 stainless steel. Scratch tracks 180, 182, 184, and 186 respectively illustrate scratch tracks created with a normal force 32 at a load of 20 mN, 25 mN, 30 mN, and 35 mN, with each scratch tracking having a scratch length of approximately 500 μm. Scratch tip 12 employed to generate the scratch tracks included a spherical tip 54 having a 5 μm radius 56 and was moved laterally at a scratch velocity 34 of 10 μm/sec.

Each scratch track comprises a series of delaminated regions similar to that illustrated by FIG. 6, with the series of delaminated regions forming what is referred to herein as a "bamboo" structure. In the example illustrated by FIG. 10, a normal load of 20 mN is the minimum force required to delaminate coating 20 from substrate 18 of the particular device 16 tested. In one embodiment, where five delaminated regions is the desired number of delaminated regions to be attained, a normal load of 30 mN corresponding to scratch track 184 would be selected as the desired constant load to employ as normal force 30 for testing device 16.

It is noted that a number of delaminated regions in a bamboo structure of a given scratch track generally decreases with increasing normal force, while an area of each of the individual delaminated regions generally increases. Because the area generally increases with increasing normal force, the toughness of interfacial adhesion, G, as determined by Equations III and IV above, remains substantially constant over a range of normal loads. As such, the magnitude of the load employed by constant normal force 30 does not substantially impact calculated values of the toughness of interfacial adhesion between coating 20 and substrate 18 as long as normal force 30 is at least equal to a minimum scratch load required to fracture and delaminate coating 20 from substrate 18.

In one embodiment, in lieu of performing scratch operations at a single desired constant load, scratch operations are carried out a plurality of normal loads, such as illustrated by FIG. 10. In such an embodiment, the toughness of adhesion of coating 20 to substrate 18 is calculated for each of the individual delaminated regions of each scratch track, such as each of the individual delaminated regions of scratch tracks 180, 182, 184, and 186, as described above with respect to Equations I, II, and IV. A toughness of interfacial adhesion between coating 20 and substrate 18 is then determined by finding an average toughness of interfacial adhesion of all delaminated regions of all the scratch tracks.

It is also noted that, through experimentation, scratch velocity 34 was found to have negligible impact on calculated values of the toughness of interfacial adhesion. It was found that increasing scratch velocity 34 results in a decrease in the area of corresponding delaminated region. However, the calculated toughness of interfacial adhesion for a given device 16 remained substantially constant at various scratch velocities 34 as the proportionality between an area of a delaminated region (see Equation I) and interfacial energy ($E_{INTERFACIAL}$) corresponding to the delaminated region (see Equation III) remains substantially constant.

Figure 11:
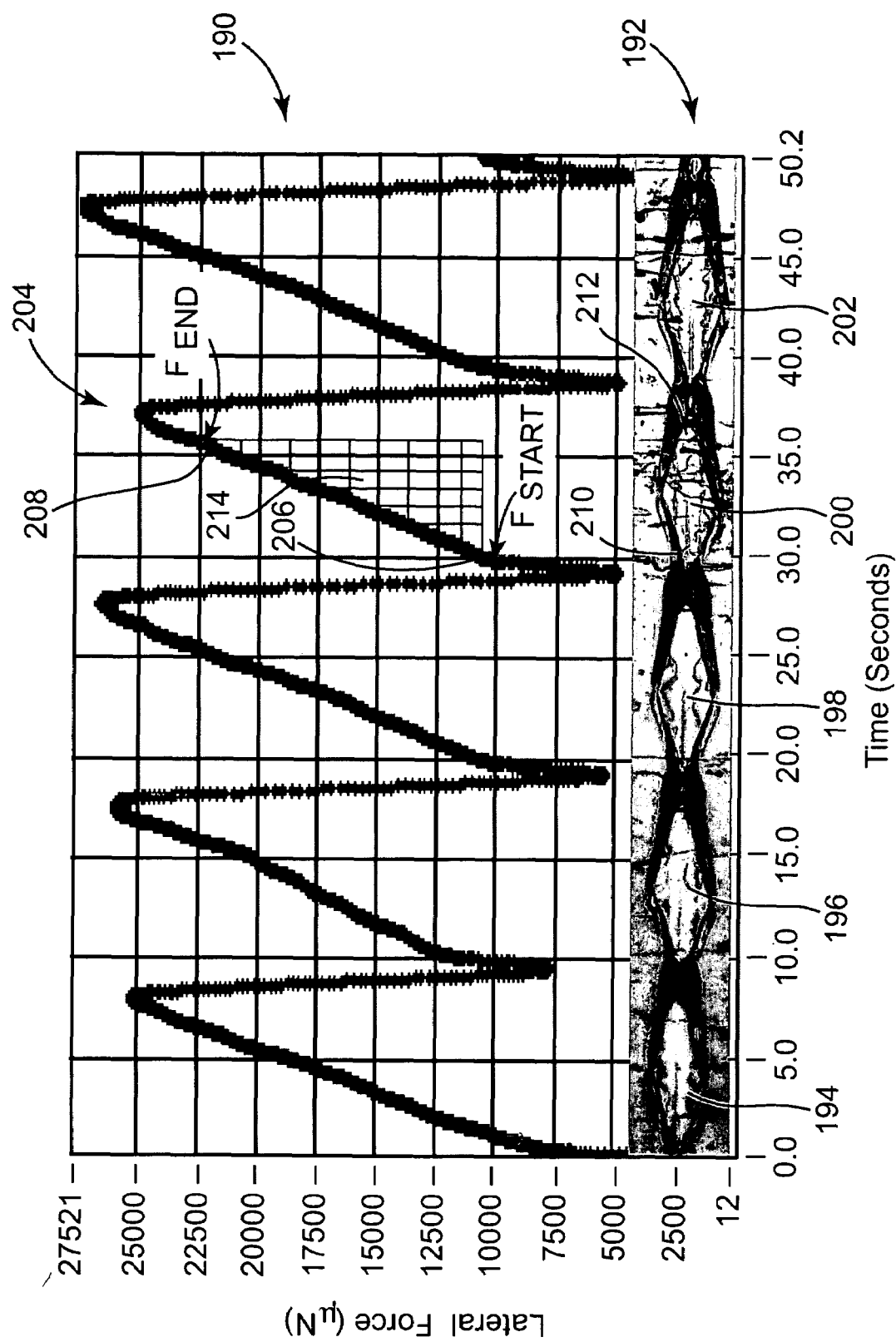
FIG. 11 illustrates a graph of lateral force versus time on a scratch probe and an image of a corresponding scratch track in a coating on a device.

FIG. 11 illustrates the relationship between lateral force 32 and corresponding delaminated regions created in coating 20 of a tested device 16. FIG. 11 includes a graph 190 of lateral force 32 resulting from a scratch probe 12 applying a constant 30 mN normal force to and moving laterally across device 16 at a scratch velocity of 10 µm/sec. An optical micrograph provided by imaging device 26 illustrates a corresponding scratch track 192 comprising a series of delaminated regions 194, 196, 198, 200, and 202 and which is time-wise aligned with graph 190.

As illustrated, each oscillation or delamination cycle of lateral force 32 of graph 190 corresponds to a delaminated region of scratch track 192. For example, a scratch cycle 204 corresponds to delaminated region 200 with $F_{START}$ 206 and $F_{END}$ 208 aligning respectively with a beginning point 210 and an ending point 212 of delaminated region 200. The interfacial energy ($E_{INTERFACIAL}$) required to form delaminated region 200 is equal to an area of triangular-shaped region 214 multiplied by scratch velocity (V) 34.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A method for measuring toughness of interfacial adhesion, the method comprising:
    applying a normal force with a probe to a surface of a coating joined to a major surface of a substrate of a medical device, wherein the surface is substantially parallel to the major surface;
    applying a lateral force to the coating with the probe by laterally moving a position of the probe relative to the major surface such that the probe forms at least one delaminated region in the coating as the position of the probe moves laterally across the major surface, the delaminated region having a starting point and an ending point;
    measuring a magnitude of the lateral force over time;
    determining a toughness of interfacial adhesion between the coating and the major surface based on changes in magnitude of the lateral force as the position of the probe moves from the starting point to the ending point.

2. The method of claim 1, wherein the probe comprises a configuration which is substantially symmetrical about a longitudinal axis.

3. The method of claim 1, wherein the probe comprises a cono-spherical configuration.

4. The method of claim 1, further including:
    measuring a normal displacement of the probe relative to the major surface as the position of the probe moves laterally relative to the major surface; and
    determining the starting point and the ending point based on the normal displacement.

5. The method of claim 1, wherein the starting point corresponds to a point of initial fracture of the coating.

6. The method of claim 1, wherein the ending point corresponds to a point where a portion of coating separated from the major surface by the scratch tip to form the delaminated region ceases to separate from the major surface.

7. The method of claim 1, wherein determining the toughness of interfacial adhesion further includes determining an amount of interfacial energy based on increases in magnitude of the lateral force as the position of the probe moves from the starting point to the ending point, wherein the increases are relative to a magnitude of the lateral force when the probe is at the starting point.

8. The method of claim 1, wherein determining the toughness of interfacial adhesion further includes:
    determining an area of the delaminated region; and
    dividing the amount of interfacial energy by the area of the delaminated region.

9. The method of claim 1, wherein applying the normal force further includes applying the normal force at a substantially constant magnitude.

10. The method of claim 9, wherein applying the normal force includes applying at a substantially constant magnitude which causes the probe to form a desired number of delaminated regions in a desired distance across the major surface.

11. The method of claim 1, wherein applying the normal force further includes applying the normal force at a magnitude which increases over time.

12. The method of claim 1, wherein applying the lateral force includes moving the position of the probe such that the probe forms a series of delaminated regions in the coating with each delaminated region having a beginning point and an ending point.

13. The method of claim 12, wherein determining a toughness of interfacial adhesion between the coating and major surface includes:
    determining a toughness of interfacial adhesion for each delaminated region of the series of delaminated regions; and
    determining a toughness of interfacial adhesion between the coating and the major surface of the substrate of the medical device by averaging the toughness of interfacial adhesion of a selected portion of the series of delaminated regions.

14. A system for measuring a toughness of interfacial adhesion of coatings on medical devices, comprising:
    a probe;
    a controller configured to cause the probe to apply a normal force to a surface of a coating applied to a major surface of a substrate of a medical device, wherein the surface is substantially parallel to the major surface, and configured to cause the probe to apply a lateral force to the coating by laterally moving a position of the probe relative to the surface so as to cause the probe to form at least one delaminated region in the coating, wherein the delaminated region has a starting point and an ending point;
    a force sensor configured to measure a magnitude of the lateral force over time; and
    an analyzer module configured to determine a toughness of interfacial adhesion between the coating and the major surface based on increases in the measured magnitudes of the lateral force as the probe moves from the starting point to the ending point.

15. The system of claim 14, wherein the controller is configured to measure a normal displacement of the probe relative to the surface as the position of the probe moves laterally relative to the surface, and wherein the analyzer module is configured to determine the starting point and the ending point based on the normal displacement.

16. A system for measuring a toughness of interfacial adhesion of coatings on medical devices, comprising:
a probe;
a controller configured to cause the probe to apply a normal force to a surface of a coating applied to a major surface of a substrate of a medical device, wherein the surface is substantially parallel to the major surface, and configured to cause the probe to apply a lateral force to the coating by laterally moving a position of the probe relative to the surface so as to cause the probe to form at least one delaminated region in the coating, wherein the delaminated region has a starting point and an ending point;
a force sensor configured to measure a magnitude of the lateral force over time; and
an analyzer module configured to determine a toughness of interfacial adhesion between the coating and the major surface based on increases in the measured magnitudes of the lateral force as the probe moves from the starting point to the ending point, wherein the controller is configured to measure a normal displacement of the scratch probe, and wherein the analyzer module is configured to determine the starting point and the ending point based on slope changes in measured values of the normal displacement of the scratch probe.

17. The system of claim 14, wherein the controller is configured to control and measure a lateral velocity of the probe with respect to the medical device.

18. The system of claim 14, wherein the analyzer comprises a portion of the controller.

19. The system of claim 14, wherein the probe comprises a probe having a configuration which is substantially symmetrical about a longitudinal axis.

20. The system of claim 14, wherein the probe comprises a probe having a cono-spherical configuration.

21. The system of claim 14, further comprising an imaging device configured to provide an image of the coating, including the delaminated region.

22. The system of claim 14, wherein the imaging device includes a measurement module configured to determine an area of the delaminated region.

23. A method of measuring properties of interfacial adhesion, the method comprising:
applying a normal force to a surface of a thin-film joined to a major surface of a medical device, wherein the surface is substantially parallel to the major surface;
applying a lateral force to the coating relative to the surface so as to separate a portion of the coating from the major surface to form a delaminated region, the delaminated region having a starting point and an ending point;
measuring a magnitude of the lateral force over time; and
determining a toughness of interfacial adhesion between the coating based on increases in the measured magnitudes of the lateral force during a time period required to form the delaminated region from the starting point to the ending point, wherein the increases in measured magnitudes of the lateral force are relative to a measured magnitude of the lateral force at a time corresponding to the beginning of the time period.

* * * * *

UNITED STATES PATENT AND TRADEMARK OFFICE
CERTIFICATE OF CORRECTION

PATENT NO. : 7,287,420 B2
APPLICATION NO. : 11/316471
DATED : October 30, 2007
INVENTOR(S) : Dehua Yang et al.

Page 1 of 1

It is certified that error appears in the above-identified patent and that said Letters Patent is hereby corrected as shown below:

Column 1, line 29, delete "or "Blister test," and insert in place thereof --or "Blister" test--.

Column 9, line 40, delete "Equation I:" and insert in place thereof --Equation II:--.

Column 10, line 22, delete "$x_i$ ᵢ" and insert in place thereof --$x_i$--.

Signed and Sealed this

Seventeenth Day of June, 2008

JON W. DUDAS
*Director of the United States Patent and Trademark Office*